United States Patent
Booth, Jr. et al.

(10) Patent No.: US 6,183,470 B1
(45) Date of Patent: Feb. 6, 2001

(54) INSTRUMENTATION FOR THE PREVENTION OF EMBOLISMS DURING TOTAL JOINT ARTHROPLASTY

(75) Inventors: Robert E. Booth, Jr., Philadelphia, PA (US); Gregory C. Stalcup, Columbia City, IN (US)

(73) Assignee: Bristol-Myers Squibb Company; by said Gregory Stalcup ( * ) Notice: Under 35 U.S.C. 154(b), the term of this patent shall be extended for 0 days.

(21) Appl. No.: 09/346,851

(22) Filed: Jul. 2, 1999

(51) Int. Cl.⁷ .................................................. A61B 17/56
(52) U.S. Cl. ................................................. 606/53; 606/62
(58) Field of Search .................................. 606/53, 60, 62, 606/86, 96

(56) References Cited

U.S. PATENT DOCUMENTS

| | | | | |
|---|---|---|---|---|
| 5,192,282 | * | 3/1993 | Draenert | 606/65 |
| 5,312,408 | * | 5/1994 | Brown | 606/80 |
| 5,707,374 | * | 1/1998 | Schmidt | 606/85 |
| 5,766,180 | * | 6/1998 | Winquist | 606/62 X |
| 5,814,049 | * | 9/1998 | Pratt et al. | 606/80 |
| 6,019,761 | * | 2/2000 | Gustilo | 606/62 |

FOREIGN PATENT DOCUMENTS

1806654 * 4/1993 (SU) ........................................ 606/62

* cited by examiner

*Primary Examiner*—Jeffrey A. Smith
(74) *Attorney, Agent, or Firm*—Todd A. Dawson

(57) ABSTRACT

The invention herein describe reduces the concerns associated with the use of intramedullary instrumentation by providing for the reduction of pressure within the medullary canal as the intramedullary instrument is inserted. Specifically, in the preferred embodiment a sleeve having a proximal end connected to a vacuum source is fitted over the intramedullary rod so that as the rod is inserted into the intramedullary canal, the pressure within the canal is reduced to thereby reduce the magnitude of cells released into the blood stream. In order to draw air from the medullary canal, the proximal end of the sleeve includes a gasket which seal against the intramedullary rod causing the air to be drawn only from the distal end of the sleeve. In an alternative embodiment, an air passage is provided directly through the instrument with the exposed end of the instrument being connected to a vacuum source.

3 Claims, 3 Drawing Sheets

INSTRUMENTATION FOR THE PREVENTION OF EMBOLISMS DURING TOTAL JOINT ARTHROPLASTY

FIELD OF THE INVENTION

This invention relates to instrumentation used during the implantation of prosthetic joint components and has specific relevance to a device which reduces the pressure within an intramedullary canal for the prevention of embolisms during surgery.

BACKGROUND OF THE INVENTION

During total joint arthroplasty, instrumentation is used by the surgeon to align various cutting or milling guides relative to the bone and the natural joint line. This instrumentation is well known in the art and need not be discussed in any detail here. In general, there are two classes of instruments for use during surgery, intramedullary and extramedullary. Extramedullary instrumentation is design to be position outside of the patients bone and is usually affixed to the patients limb by a series of straps or pins. Intramedullary devices are designed to be positioned directly within the medullary canal of the bone and generally include an elongate rod which is pushed into the medullary canal. Since the intramedullary instruments are positioned within the bone to receive the joint, they are generally considered more accurate than extramedullary instrumentations.

However, one draw back to the use of intramedullary instrumentation is the potential to cause fat cells within the medullary canal to be displaced during insertion of the intramedullary rod of the instrument. This issue becomes especially problematic if a bi-lateral knee procedure is being performed which would require an intramedullary rod be inserted into the medullary canal of both femurs and both tibial. To reduce the concerns discussed above, surgeons often choose to use extramedullary instrumentation or to perform surgery on one knee at a time. By delaying a needed surgery on the other malfunctioning knee, the patient is required to undergo two separate surgery sessions.

The use of stemmed provisional implant to test the fit and position of the final implant also may further add to the build up of pressure within the femoral canal. It would not be unusual for a stemmed tibial and femoral provisional components to be inserted into the intramedullary canals of the prepared tibia and femur multiple times during a surgery to test the fit and anatomic functionality of the final implant. The stemmed components may create a build up of pressure within the intramedullary canal. As it is impossible to replicate these components in an extramedullary solution, the surgeon may be forced to delay the operation on the patients second knee if stemmed components will be required.

SUMMARY OF THE INVENTION

The invention herein describe reduces the concerns expressed above associated with the use of intramedullary instrumentation by providing for the reduction of pressure within the medullary canal as the intramedullary instrument is inserted. Specifically, in the preferred embodiment a sleeve having a proximal end connected to a vacuum source is fitted over the intramedullary rod so that as the rod is inserted into the intramedullary canal, the pressure within the canal is reduced to thereby reduce the magnitude of cells released into the blood stream. In order to draw air from the medullary canal, the proximal end of the sleeve includes a gasket which seal against the intramedullary rod causing the air to be drawn only from the distal end of the sleeve. In an alternative embodiment, an air passage is provided directly through the instrument with the exposed end of the instrument being connected to a vacuum source.

Regarding the provisional instruments, the purpose behind such instruments is to provide the surgeon the proper feedback to ensure that the final implant will fit properly within the prepared bone. Therefore, it is impractical to provide a sleeve about the provisional stems as it would add to the outer diameter of the provisional. Therefore, this invention contemplates providing a set of provisional stems having an air passage provided therethrough for connection to a vacuum source.

Accordingly, it is an object of this invention to provide for instrumentation for use in orthopaedic surgery having an air passage or vent means for connection to a vacuum source to enable the intramedullary pressure to be reduced as the instrument is inserted therein.

Another object of this invention is to provide for a sleeve for accommodating an intramedullary rod of an orthopaedic instrument, wherein one end of the sleeve is connected to a vacuum source and the distal end include slots forming a vent.

Yet another object of this invention is to provide for instrumentation for use in orthopaedic surgery having an air passage or vent means formed through the instrument for connection to a vacuum source to enable the intramedullary pressure to be reduced as the instrument is inserted therein Still other objects of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they is chosen and described to enable others skilled in the art to utilize the teachings of the invention.

Figure 1:
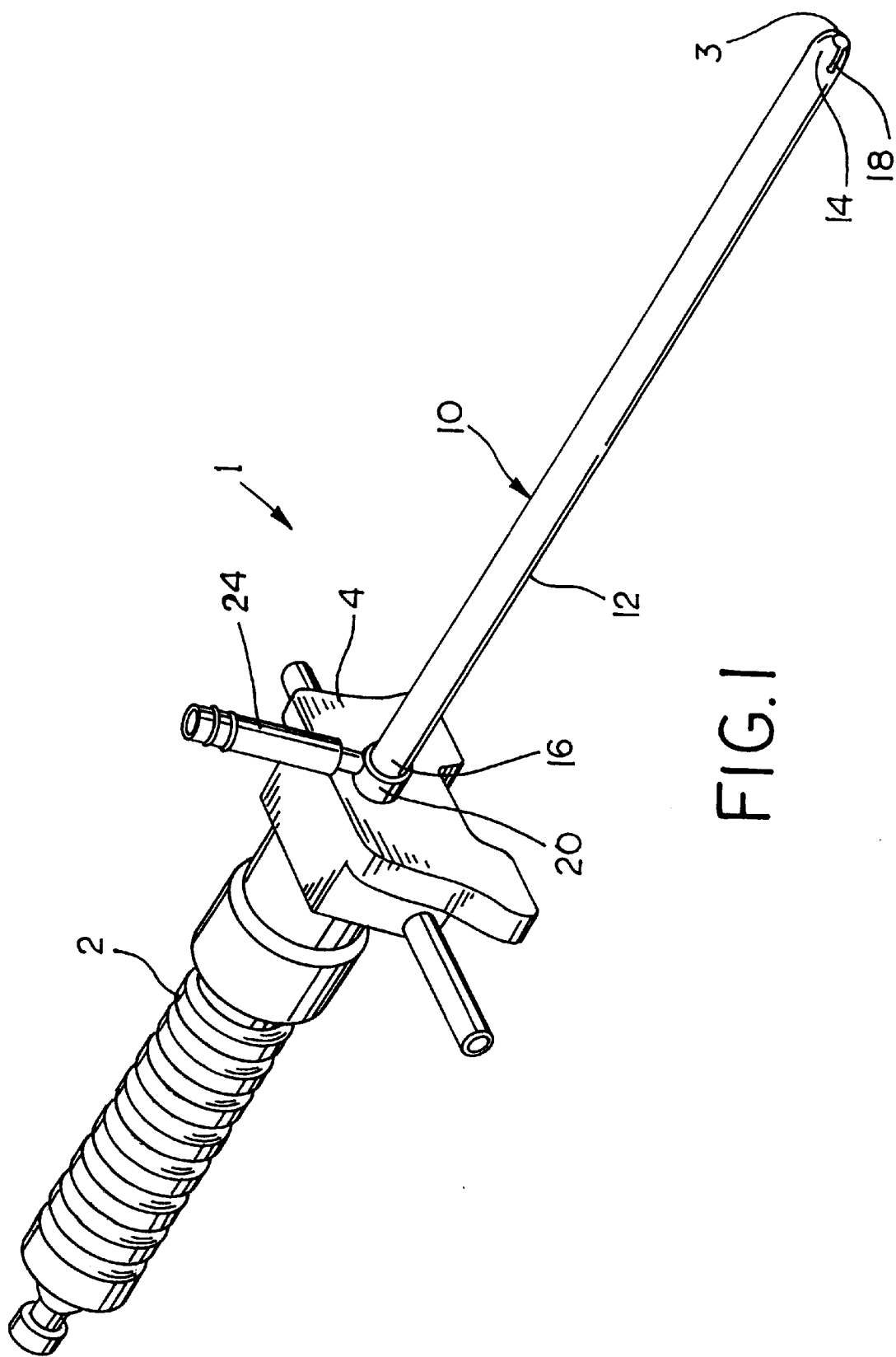
FIG. 1 is a perspective view of an intramedullary instrument of the type used in a total knee with the sleeve of the invention fitted over the rod portion of the instrument. This figure is used to illustrate the environment of the invention.

Referring to FIG. 1 and typical instrument for use in orthopaedic knee replacement surgery is illustrated. The particular instrument illustrated is adapted for use with the femur. Instrument 1 includes a handle portion 2 and a intramedullary (IM) rod 3 as well as a reference base 4. In use the IM rod 3 is inserted into the prepared intramedullary rod of the femur and the base 4 provide a reference point for other instrumentation or cutting guides. It should be obvious that the particular instrument illustrated in FIG. 1 is provided solely for the purpose of illustrating the environment of the invention and should not be considered limiting the scope of the invention.

Figure 2:
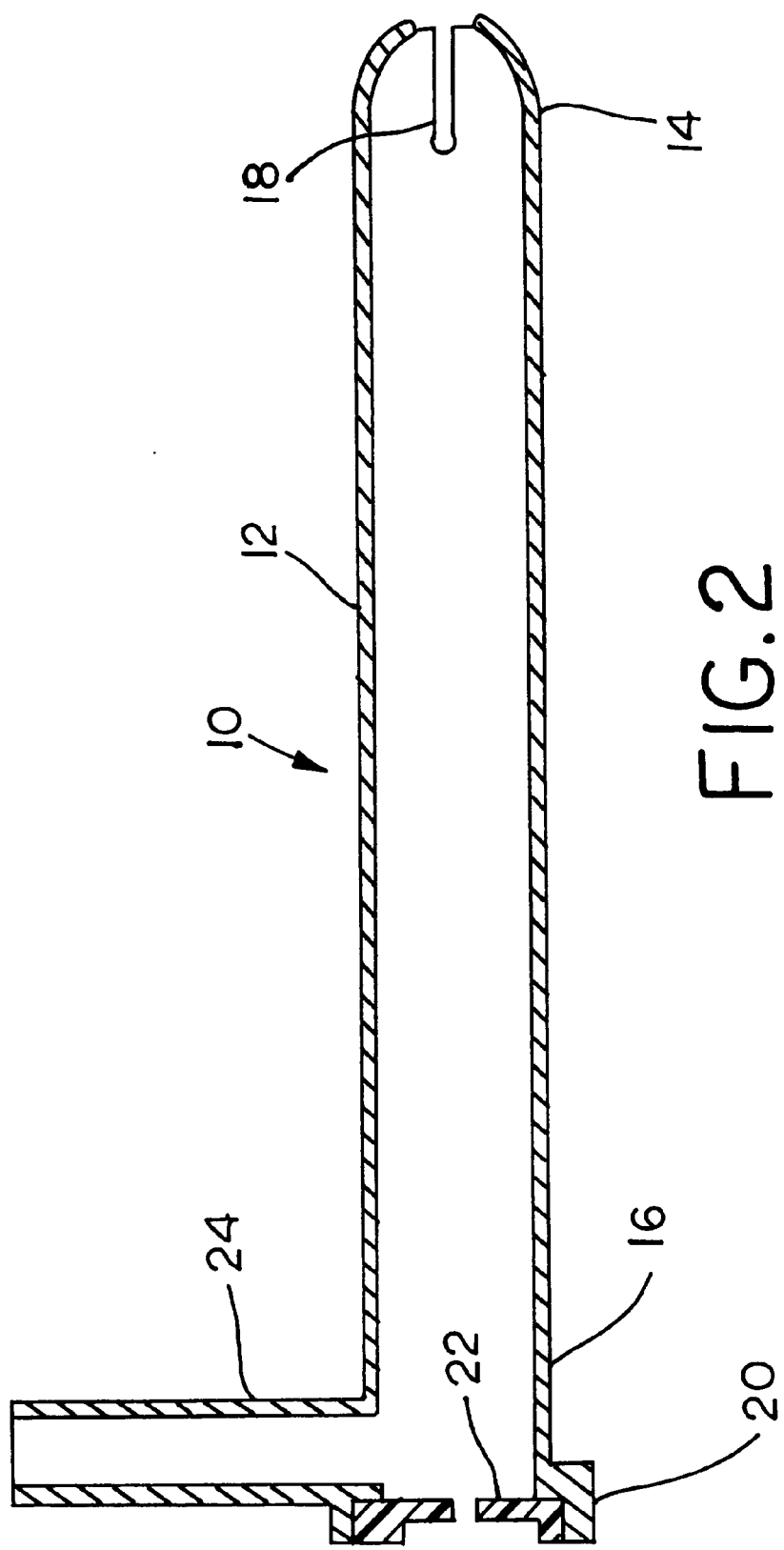
FIG. 2 is a side elevational view of the sleeve of the invention with portions sectioned for illustrative purposes.

Continuing to refered to FIG. 1 and with reference to FIG. 2, sleeve 10 of the invention includes an elongate tubular body 12 having a first end 14 and a second end 16. End 14 includes a plurality of slots 18 and is rounded slightly for easier insertion into the intramedullary canal of the femur (not shown). The second end 16 includes an annular ring housing 20 which is sized to accommodate a gasket 22. Gasket 22 carried within housing 20 is configured to form a seal against the outer periphery of the rod 3 of instrument 1 during use. A vacuum port 24 is connected in flow communication with body 12 adjacent housing 20 and includes a plurality of annular detents around its exterior as illustrated.

In use, sleeve 10 is slipped onto rod 3 such that the first end 14 is adjacent the end of the rod 3 and such that end 16 is adjacent base 4. Gasket 22 contacts rod 3 to form a seal against the rod. Tubular body 12 of sleeve 10 is slightly larger in diameter than rod 3 which forms an air passage therebetween. A vacuum hose (not shown) which is connected at one end to a vacuum source is attached to vacuum port 24. After the vacuum source is initiated, the surgeon advances the IM rod 3 with sleeve 10 attached into the intramedullary canal of the femur. As the sleeve and rod advances, the vacuum draws air through slots 18, air passage 19 and out vacuum port 24. In this manner, as the rod and sleeve is advanced, pressure is pulled out of the canal and not allowed to build up. Therefore, cells within the canal will not be pushed into the patients circulatory system. Alternatively, the sleeve 10 could be fully inserted into the intramedullary canal with the suction source attached and then insert the IM rod 3 into the sleeve. Either method will be sufficient to reduce the pressure within the canal as set forth in this invention.

Figure 3:
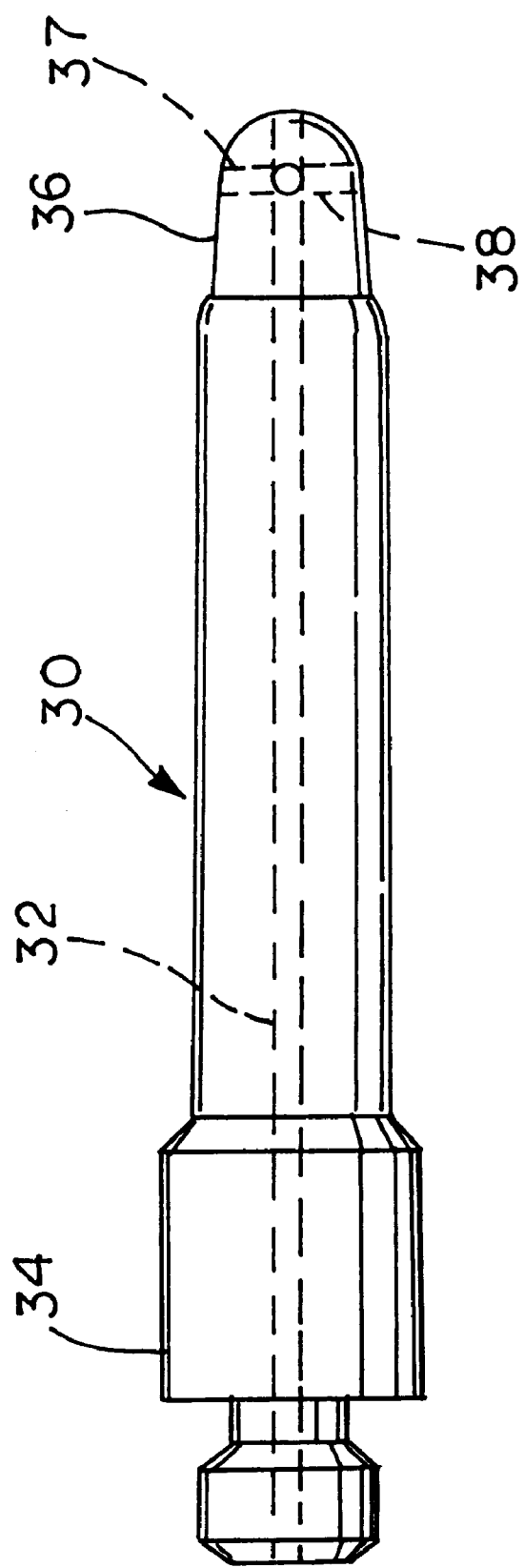
FIG. 3 is a sectional view of the stemmed provisional instrument of the invention.

FIG. 3 illustrates a provisional implant stem 30 which is an instrument used during an orthopaedic surgery to test fit a provisional implant to the bone. Provisional implants are used by surgeons to provide a visual indication of the fit of the eventual implant and to provide feedback as the status of the reconstructed joint structure. Therefore, it would not be unusual for a stemmed provisional to be inserted repeatedly in a surgery as the fit of the implant is perfected. Therefore, the provisional stem 30 of this invention includes a vent 32 formed therethrough from a proximal end 34 to its distal end 36. The vent 32 runs longitudinally within the stem and may include one or more axial vent shafts 38. In use, the proximal opening of the vent shaft is connected to a vacuum source as the stem 30 and its associated implant is inserted into the intramedullary canal of a bone to reduce the pressure within the canal.

It should be understood that yet another embodiment of the invention could be the formation of a vent passage directly through the IM rod 3 of FIG. 1. However, it is believe that while that embodiment would satisfy the intent of the invention, the manufacturing such and instrument may be difficult.

It should be also understood that the invention is not limited to the precise forms disclosed. Rather it may be modified within the keeping of the appended claims.

We claim:

1. An instrument for use in orthopaedic surgery to reduce the pressure within an intramedullary canal of a bone, said instrument including a tubular body having a first end and a second end, said first end including a suction port being configured for connection to a vacuum source, said second end being configured for insertion into an intramedullary canal, said suction port and second end being in flow communication, wherein said tubular body is configured for carrying an intramedullary rod therein, said first end including a seal configured for contacting said intramedullary rod, wherein upon said suction port being connected to a suction source, air flows from said second end through said tubular body and out said suction port.

2. A sleeve for use in orthopaedic surgery in combination with an orthopaedic instrument having an intramedullary rod, said sleeve including a tubular body having a first end and a second end, said first end including a suction port being configured for connection to a vacuum source, said second end being configured for insertion into an intramedullary canal, said suction port and second end being in flow communication, wherein said tubular body is configured for carrying said intramedullary rod therein, said first end including a seal configured for contacting said intramedullary rod, wherein an air path is formed between said tubular body and said intramedullary rod extending from said second end to said seal and in flow communication with said vacuum port, wherein upon said suction port being connected to a suction source, air flows from said second end through said air path and out said suction port.

3. The instrument of claim 2 wherein said second end includes a plurality of slots.

* * * * *